United States Patent
Greenleaf et al.

(10) Patent No.: US 9,044,192 B2
(45) Date of Patent: Jun. 2, 2015

(54) SYSTEM AND METHOD FOR NON-INVASIVELY MEASURING TISSUE VISCOELASTICITY USING SURFACE WAVES

(75) Inventors: James F. Greenleaf, Rochester, MN (US); Mark R. Pittelkow, Rochester, MN (US); Randall R. Kinnick, Rochester, MN (US); Xiaoming Zhang, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 653 days.

(21) Appl. No.: 12/418,111

(22) Filed: Apr. 3, 2009

(65) Prior Publication Data

US 2010/0010346 A1    Jan. 14, 2010

Related U.S. Application Data

(60) Provisional application No. 61/042,814, filed on Apr. 7, 2008.

(51) Int. Cl.
*A61B 8/00* (2006.01)
*A61B 5/00* (2006.01)

(52) U.S. Cl.
CPC .............. *A61B 5/442* (2013.01); *A61B 5/0051* (2013.01)

(58) Field of Classification Search
USPC ............ 600/407, 437, 438, 587; 73/584, 589, 73/597, 599, 602
See application file for complete search history.

(56) References Cited

U.S. PATENT DOCUMENTS

| | | | | |
|---|---|---|---|---|
| 3,696,313 | A * | 10/1972 | Adler | 333/150 |
| 4,362,058 | A * | 12/1982 | Abele | 73/599 |
| 4,777,599 | A * | 10/1988 | Dorogi et al. | 600/552 |
| 4,947,851 | A * | 8/1990 | Sarvazyan et al. | 600/438 |
| 5,054,502 | A * | 10/1991 | Courage | 600/587 |
| 5,095,465 | A * | 3/1992 | Stokoe, II | 367/14 |
| 5,115,808 | A * | 5/1992 | Popovic et al. | 600/438 |
| 2005/0283073 | A1 * | 12/2005 | Hoff et al. | 600/437 |
| 2006/0211943 | A1 * | 9/2006 | Beaupre | 600/471 |

OTHER PUBLICATIONS

E.C. Ruvolo Jr.; Skin Viscoelasticity Displays Site- and Age-Dependent Angular Anisotropy; Skin Pharmacol Physiol 2007;20:313-321.
Akiva Vexeler, et al; Evaluation of Skin Viscoelasticity and Anisotropy by Measurement of Speed of Shear Wave Propagation With Viscoelasticity Skin Analyzer1; Copyright © 1999 by the Society for Investigative Dermatology, Inc.; 8 pages.

* cited by examiner

*Primary Examiner* — Unsu Jung
*Assistant Examiner* — Michael N Fisher
(74) *Attorney, Agent, or Firm* — Quarles & Brady, LLP

(57) ABSTRACT

A system and method for assessing tissue health based on the viscoelastic properties of the tissue. Surface waves are induced in the tissue and their propagation characteristics are then measured. The tissue viscoelastic properties are then determined from the surface wave measurements using a surface model.

20 Claims, 4 Drawing Sheets

SYSTEM AND METHOD FOR NON-INVASIVELY MEASURING TISSUE VISCOELASTICITY USING SURFACE WAVES

CROSS REFERENCE TO RELATED APPLICATIONS

This application is based on, claims the benefit of, and incorporates herein by reference U.S. Provisional Application Ser. No. 61/042,814, filed Apr. 7, 2008, entitled "SYSTEM AND METHOD FOR NON-INVASIVELY MEASURING TISSUE VISCOELASTICITY USING SURFACE WAVES."

FIELD OF THE INVENTION

The present invention relates to systems and methods for analyzing tissue in-vivo and, more particularly, to systems and methods for analyzing tissue using surface waves that propagate through the tissue.

BACKGROUND

Elastic properties of tissue have generated considerable interest in medicine due to their clinical relevance in identifying, quantifying the severity of, and monitoring the progression of diseases. Tissue elastic properties also serve as biomarkers for cancer, since malignancies are typically more firm by palpation.

In dermatology, for example, the mechanical properties of skin are known to vary between different anatomical regions. The mechanical properties are generally age-dependent and are influenced by different physiological conditions as well as skin disease. One such disease is scleroderma, or systemic sclerosis (SSc), a chronic connective tissue disease often accompanied by a thickening or hardening of the skin as the dermis becomes infiltrated with collagen. Subdermal connective tissue sclerosis leads to dermal tethering and reduced skin mobility. SSc is a multi-system disease also characterized by visceral fibrosis. Accordingly, SSc can cause serious damage to internal organs including the lungs, heart, kidneys, esophagus, and gastrointestinal tract. In fact, cardiac involvement is a common finding in SSc and clinical evidence of myocardial disease may be found in 20-25% of SSc patients. At postmortem examination the heart is affected in up to 80% of patients. Thus, skin disease is both a disabling feature of SSc and a predictor of visceral involvement and increased mortality. Accordingly, an improvement in skin disease correlates with improved survival.

Imaging methods such as confocal microscopy, cutaneous ultrasound, and magnetic resonance imaging (MRI) may be used to analyze tissue for conditions like SSc. Confocal microscopy provides an excellent spatial resolution of about 1 µm and highly efficient visualization of the stratum corneum, but has decreased signal-to-noise ratios (SNRs) when imaging the inner layers of the epidermis. The application of MRI to dermatology has become practical with the advent of specialized surface coils that act as sensitive receivers for signals produced by superficial structures. MRI can provide in-depth resolution on the order of 35 to 70 µm, allowing clear delineation and analysis of the epidermis, but is limited by its high cost and large equipment. Cutaneous ultrasound is a high-frequency ultrasound imaging technique that provides an axial resolution on the order of 30 to 60 µm. Current dermatologic A-scan and B-scan ultrasound units, which operate at frequencies of 15-25 MHz (versus 2-10 MHz for internal medical applications), are capable of distinguishing objects only 50 µm thick while surveying skin to a depth of 1 to 2 cm. Several important uses of cutaneous ultrasound have been investigated, including the measurement of skin thickness, assessment of mass lesions, and the general noninvasive evaluation of skin structure and function. While the epidermis and adnexal structures may generally be seen using dermatological ultrasound, cellular features such as the stratum corneum and basal-cell layers cannot be readily distinguished.

Other methods, such as indentometry, ballistometry, twistometry, and the suction method, analyze tissue mechanical properties to assess tissue health. Measurement of skin mechanical properties has been applied to various medical and cosmetic applications, including the evaluation of laser-based skin resurfacing techniques, the relationship between skin elasticity and wrinkle levels, the role of fibroblast integrins $\alpha 2$ and $\beta 1$ in maintaining dermal skin properties, and cutaneous alterations in children with growth hormone deficiencies. The mechanical properties of skin have also been used to study the facial skin elasticity of diabetic patients and human skin fatigue.

Ballistometry, which was originally developed for evaluating the density of metallic surfaces, is a biomechanical technique in which cutenoues tone is assessed by analyzing the rebound of a light weight from a tissue surface. Plasticoelastic consequences of diseases such as psoriasis, dermal sclerosis, and aging can be analyzed using ballistometry. Twistometry employs a disk that is glued to the skin and rotated to load a selected level of torque onto underlying skin. The angle of twist of the skin around the disk is then measured to determine skin stiffness.

Commercially available devices, such as the Dermaflex and Cutometer, use the suction method to measure skin displacement caused by a suction force exerted over a defined area of the skin. The Dermaflex device is commercially available from Cortex Technology, Hadsund, Denmark. Cutometer is a registered trademark of Courage+Khazaka Electronic GMBH Corporation of Germany. The Dermaflex device determines skin displacement by measuring the electrical capacitance between the skin surface and an electrode placed on top of the suction device. The Cutometer device measures skin displacement using an optical system. The Dermaflex device has large aperture diameter of 10 mm, while the Cutometer device has a variety of probes with aperture diameters ranging between 1 and 8 mm. It is generally thought that larger aperture diameters measure deeper layers of skin and smaller aperture diameters measure superficial skin layers.

The established method of skin assessment is the Rodnan skin score (RSS), from which the modified Rodnan skin score (MRSS) has more recently been developed. Both RSS and MRSS use semi-quantitative manual skin scoring. For example, using the MRSS method, skin properties such as thickness and stiffness are assessed via palpitation and scored using a 4-degree scale. This is performed for 17 regions of the body, leading to a maximum score of 51. Both RSS and MRSS methods can be subject to observer bias and intraobserver and interobserver variabilities of 12 and 25 percent, respectively. Also problematic is the need for investigator training, varying degrees of examiner experience, and uncertainty about the sensitivity of the scores to change over time.

The above-described methods for assessing the mechanical properties of skin have many limitations that reduce their diagnostic value. For example, their measurements are typically dependent on probe size and application and are generally not indicative of subcutaneous tissue's effects on the skin. Accordingly, assessments of tissue health can vary strongly between patients and observers.

It would therefore be desirable to have a system and method for measuring the dynamic mechanical properties of tissues and producing improved assessments of tissue health that are largely independent of the device used in their obtainment.

SUMMARY OF THE INVENTION

The present invention overcomes the aforementioned drawbacks by providing a system and method for assessing tissue health by producing and analyzing surface waves in the tissue to determine the tissue's viscoelastic properties. The method is quantitative, reliable, and repeatable and its measurements are independent of excitation and detection.

The present invention provides a method for analyzing a tissue using a medical device. The method comprises the steps of applying a stimulus to a selected location on the tissue to produce waves that propagate through the tissue, acquiring data indicative of a surface wave phase at a plurality of tissue locations, and estimating changes in surface wave phase with respect to distance. The method further comprises estimating a surface wave velocity from the estimated changes in surface wave phase with respect to distance, determining a viscoelastic property of the tissue from the estimated surface wave velocity, and generating a report indicative of at least one property of the tissue from the determined viscoelastic properties.

The present invention also provides a medical device for assessing the health of a tissue. The device comprises a driver configured to apply a stimulus to the tissue and produce waves that propagate through the tissue and a detector configured to acquire data indicative of surface wave phase at a plurality of tissue locations. The device further comprises a processor in communication with the detector configured to estimate changes in surface wave phase with respect to distance, estimate a surface wave speed, determine a viscoelastic property of the tissue from the estimated surface wave speed, and generate a report indicative of the health of the tissue.

Various other features of the present invention will be made apparent from the following detailed description and the drawings.

DESCRIPTION OF THE PREFERRED EMBODIMENT

Many human tissues such as skin are viscoelastic, having both the properties of viscosity and elasticity. Viscosity is related to a delayed recovery from deformation and functions as a buffer that counteracts the velocity of an external force, resulting in a delay of movement. Elasticity is related to rebounding and quick recovery from deformation. It produces a force proportional to the extent of deformation. The present invention uses a surface wave method to analyze the viscoelastic properties of a tissue and assess tissue health.

Figure 1:
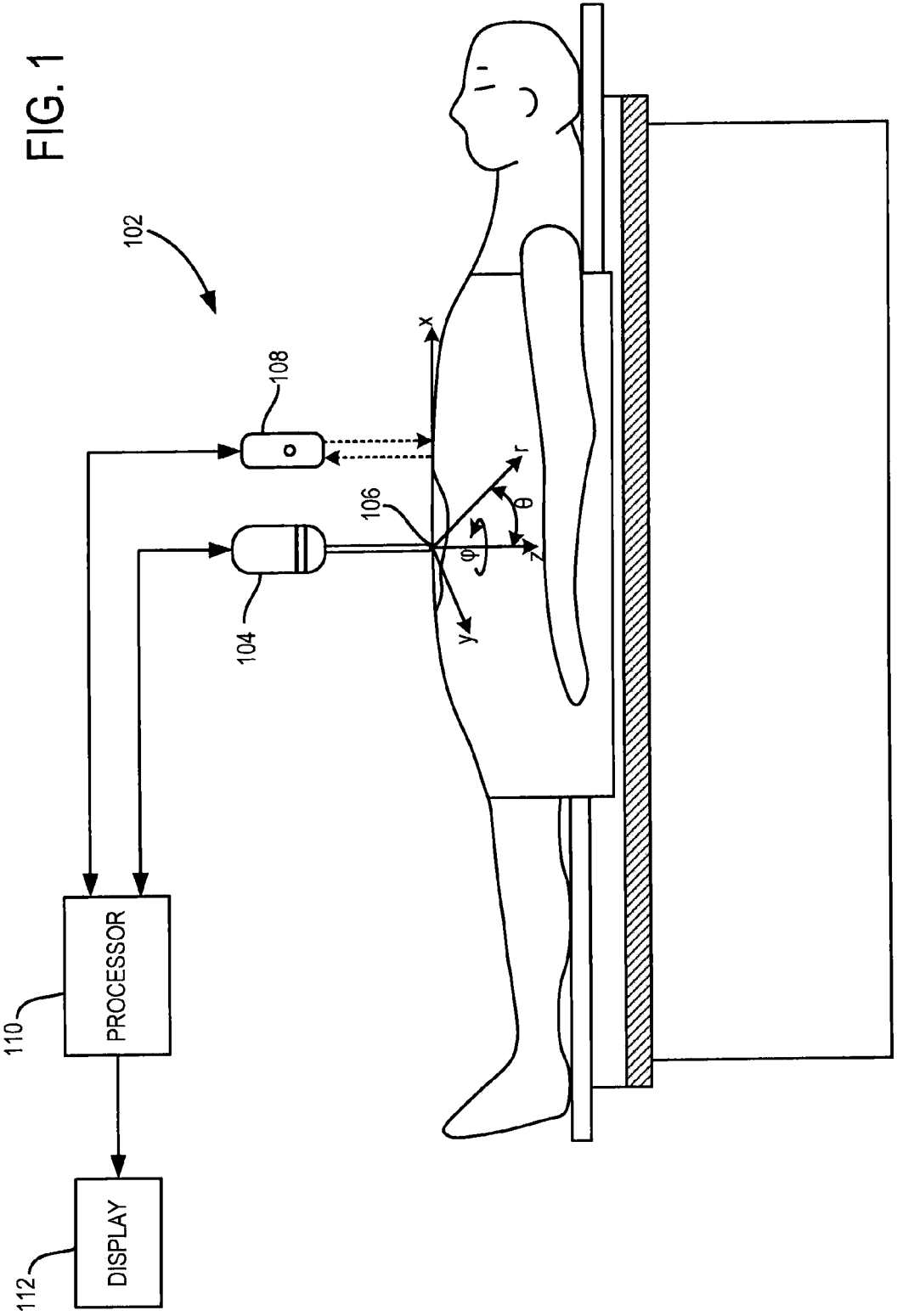
FIG. 1 is a schematic of a medical device for assessing tissue health using a single-layer surface wave model in accordance with the present invention.

Referring now to FIG. 1, the present invention employs an excitation and detection system, as indicated generally at 102, to produce and analyze surface waves on a tissue. The system 102 includes a driver 104, which provides excitation to a point of application, and a detector 108, which monitors the subject to analyze the subject tissue. The driver 104 may, for example, take the form of a transducer or mechanical shaker having a ball-tip applicator, to vibrate the tissue surface and produce a surface wave emanating with axial symmetry from the point of application 106. The frequency and force of vibration are generally selected to provide a desired signal-to-noise ratio over a given range. For example, high frequency waves decay rapidly but have shorter wavelengths that provide improved spatial resolution. It is therefore contemplated that vibrations having a force of 1 N or less may be applied at frequencies between 100 and 400 Hz.

The detector 108 is configured to measure the propagation of surface waves across the tissue. For example, a laser vibrometer detector may be employed to measure surface wave phase and amplitude at different points along the tissue surface. This advantageously provides a non-contact means of measuring surface waves so that their propagation characteristics are unaffected by the detection apparatus. This contrasts with the indentometry, ballistometry, twistometry, and suction methods, in which measurements are dependent on the detector and its application to the tissue. Ultrasound transducers can also be employed to measure wave propagation in underlying tissue layers such as subcutaneous fat and muscle layers.

The system 102 may also include a processor 110 and display 112 in communication with the excitation device 104 and detector 108 to analyze surface wave measurements, estimate tissue viscoelastic properties, and produce and display reports indicative of tissue health. For example, the processor may be configured to assess tissue health from estimates of tissue viscoelasticity, which are determined using a surface wave model and acquired surface wave properties, such as changes in surface wave phase and amplitude over a given distance. Therefore, the surface wave model and its variations will be discussed before the method for assessing tissue health.

The model may analyze surface wave propagation as wave propagation in a semi-infinite viscoelastic medium under harmonic excitation by a uniformly distributed stress on a circular surface area. The equation for wave propagation in an isotropic and viscoelastic medium is as follows:

$$\lambda + 2\mu \nabla \nabla \cdot \vec{u} - \mu \nabla x \nabla x \vec{u} = \rho \frac{\partial^2 \vec{u}}{\partial t^2}; \qquad \text{Eqn 1}$$

where $\vec{u}$ is the displacement, $\rho$ is the density of the medium, and $\lambda$ and $\mu$ are the Lamb constants of the medium. This model may be solved using a cylindrical polar coordinate system. Referring still to FIG. 1, in this model, the skin of the subject extends a long a first plane, for example, the plane extending along the x-axis and y-axis. When considering a harmonic force excitation with a uniform stress on a surface of a medium within a circular region r≤a, the integral expression for the displacement field in the r and z directions at any location in or on the medium's surface is given by:

$$u_z = \frac{a}{\mu} \int_0^\infty \frac{\sqrt{(\xi^2-1)} J_1(\xi k_1 a)}{F_0(\xi)} \left\{ \begin{array}{c} 2\xi^2 e^{-k_1 z\sqrt{(\xi^2-\eta^2)}} + \\ (\eta^2 - 2\xi^2) e^{-k_1 z\sqrt{(\xi^2-1)}} \end{array} \right\} J_0(\xi k_1 r) d\xi; \quad \text{Eqn. 2}$$

and $$u_r = \frac{a}{\mu} \int_0^\infty \frac{\xi J_1(\xi k_1 r)}{F_0(\xi)} \left\{ \begin{array}{c} 2\sqrt{(\xi^2-1)} \sqrt{(\xi^2-\eta^2)} e^{-k_1 z\sqrt{(\xi^2-\eta^2)}} + \\ (\eta^2 - 2\xi^2) e^{-k_1 z\sqrt{(\xi^2-1)}} \end{array} \right\} J_1(\xi k_1 r) d\xi; \quad \text{Eqn. 3}$$

where a is the radius of the distributed stress and $\xi$ is the integration parameter in the wave number domain, which is normalized with respect to the wavenumber for compression wave $k_1$. The divisor function of the integrated functions is:

$$F_0(\xi) = (2\xi^2 - \eta^2)^2 - 4\xi^2\sqrt{(\xi^2-1)}\sqrt{(\xi^2-\eta^2)} \quad \text{Eqn. 4;}$$

where $\eta = k_1/k_2 = \sqrt{\{2(1-\sigma)/(1-2\sigma)\}}$, $k_1 = \omega\sqrt{\rho/(\lambda+2\mu)}$, and $k_2 = \omega\sqrt{\rho/\mu}$. In the above equations, $\omega$ denotes the angular frequency, $\sigma$ is Poisson's ratio for the medium, $k_2$ denotes the wavenumber for shear wave propagation, and $J_0$ and $J_1$ denote Bessel functions of the first and second kind, respectively. It is possible to solve the wave displacement field using Eqns. 2 and 3. However, tissue elasticity can be estimated based on surface wave speed by setting the divisor function $F_0(\xi)$, to zero, which results in:

$$(2\xi^2 - \eta^2)^2 - 4\xi^2\sqrt{(\xi^2-1)}\sqrt{(\xi^2-\eta^2)} = 0 \quad \text{Eqn. 5.}$$

This is a bi-fourth equation of $\xi$, wherein the right solution for the surface wave is the only solution for which $\xi$ is real, $\xi > \eta$, and $\xi > 1$. Surface wave speed in a semi-infinite medium can be solved from Eqn. 5 for different material properties. Below, Table 1 shows ratios of wavenumbers between the shear wave and compression wave $k_2/k_1$ and that of the surface wave to compression wave $k_s/k_1$ for materials having different Poisson ratios. It shows that the surface wavenumber, which is generally close to the shear wavenumber, is the largest, while the compression wave number is the smallest. Also notable is the large range in $k_2/k_1$ and $k_s/k_1$ as the Poisson ratio varies.

TABLE 1

| Poisson's Ratio | $k_2/k_1$ | $k_s/k_1$ |
| --- | --- | --- |
| 0.25 | 1.73 | 1.88 |
| 0.33 | 2.00 | 2.14 |
| 0.40 | 2.45 | 2.60 |
| 0.45 | 3.32 | 3.50 |
| 0.49 | 7.14 | 7.49 |
| 0.50 | 22.38 | 23.43 |

The ratio of shear wave speed to surface wave speed $c_2/c_s$ is shown in Table 2 for materials having different Poisson ratios, wherein $c_2$ and $c_s$ denote shear wave speed and surface wave speed, respectively. Table 2 shows that the shear wave is slightly faster than the surface wave, but that the ratio $c_2/c_s$ is almost constant over a large range of materials. Polymer materials and soft tissues generally have a Poisson ratio between 0.45 and 0.499.

TABLE 2

| Poisson's Ratio | c2/cs |
| --- | --- |
| 0.25 | 1.09 |
| 0.33 | 1.07 |
| 0.40 | 1.06 |
| 0.45 | 1.05 |
| 0.49 | 1.05 |
| 0.50 | 1.05 |

Thus, tissue elasticity, as expressed by Young's modulus (E), can estimated from the surface wave speed using the following relationship:

$$c_s = \frac{1}{1.05}\sqrt{\frac{E}{3\rho}}; \quad \text{Eqn. 6}$$

In addition, surface wave speed may be related to shear elasticity $\mu$ by:

$$c_s = \frac{1}{1.05}\sqrt{\frac{\mu}{\rho}}; \quad \text{Eqn. 7}$$

Tissue viscosity can be measured by the decay of surface wave amplitude with distance. Because the normal displacement $u_z$ on the tissue surface can be measured using the detector 108 of FIG. 1, Eqn. 3 may be analyzed to inversely estimate tissue viscosity. The surface wave displacement $u_z$ in Eqn. 3 can be approximated in the far field by:

$$u_z \approx \frac{a^2 e^{-\frac{1}{4}i\pi}}{\mu F_0'(\xi')} \sqrt{\frac{\pi k_1 \xi'(\xi'^2-1)_1}{2r}} \left\{ 2\xi'^2 e^{-k_1 z\sqrt{(\xi'^2-\eta^2)}} + (\eta^2 - 2\xi'^2) e^{-k_1 z\sqrt{(\xi'^2-1)}} \right\} e^{-i\xi'^2 k_1 r}; \quad \text{Eqn. 8}$$

where $F'_0(\xi') = \partial F_0(\xi)/\partial \xi|_{\xi=\xi'}$ and $\xi'$ is the surface wave number. Equation 8 shows that the surface wave is a cylindrical wave that propagates with the wavenumber $\xi' k_1$. The decay rate of wave amplitude is related to the viscous part of the elastic modulus and, because the surface wave is a cylindrical wave, the wave decay effect due to geometric effect $1/\sqrt{r}$ is eliminated. The wave decay rate due to viscosity can then be calculated from wave amplitudes acquired at two locations by:

$$\gamma = -\log\left(\frac{U_z(r_2)\sqrt{r_2}}{U_z(r_1)\sqrt{r_1}}\right)/(r_2 - r_1); \quad \text{Eqn. 9}$$

where $U_z(r_1)$ and $U_z(r_2)$ are the surface wave amplitudes at locations $r_1$ and $r_2$, respectively, and $\gamma$ is the decay rate due to tissue viscosity between the two locations. The viscoelastic modulus of a tissue can then be expressed using the following complex quantity:

$$E^* = E(1+i\beta) \quad \text{Eqn. 10;}$$

where E is the real modulus without viscosity effects the viscoelastic ratio $\beta$ is related to the decay rate by:

$$\beta = 2\gamma c_s/\omega \quad \text{Eqn. 11.}$$

Alternatively, viscoelasticity may be expressed using the Voigt model $\mu(t)=\mu_1+\mu_2 \partial/\partial t$ at and wave speed dispersion with frequency, wherein $\mu_1$ is the shear elasticity and $\mu_2$ is the shear viscosity. This can be obtained by modifying Eqn. 6 as follows:

$$c_s = \frac{1}{1.05}\sqrt{\frac{2(\mu_1^2+\omega^2\mu_2^2)}{\rho(\mu_1+\sqrt{(\mu_1^2+\omega^2\mu_2^2)})}}. \quad \text{Eqn. 12}$$

Of course, it should be appreciated that a similar relationship could be derived using Eqn. 7. The wave speed dispersion can be estimated by measuring the wave speed at different frequencies, from which viscoelasticity can be estimated using a nonlinear least squares fitting technique.

Figure 2:
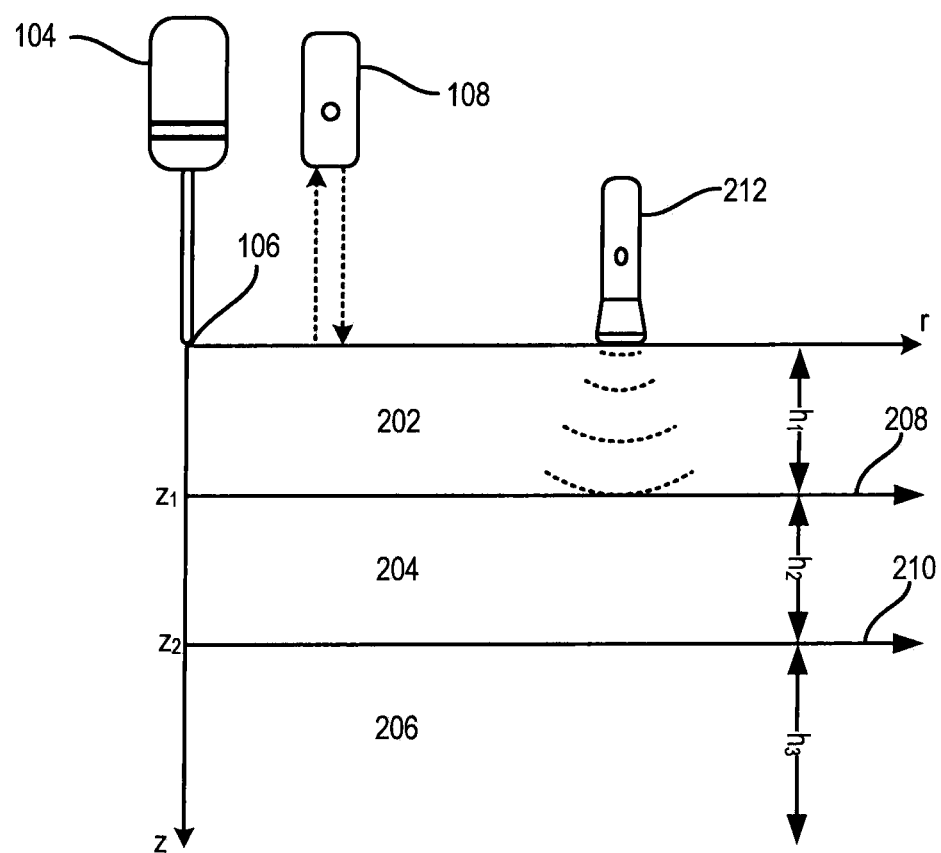
FIG. 2 is a schematic depiction of a layered skin model in accordance with the present invention.

The above-discussed surface wave model, a "single-layer" model, may be extended to analyze the influence and sensitivity of underlying tissue structures on surface wave propagation. For example, while surface wave propagation on the skin is dominated by the dermis, including the effects of subcutaneous tissue on surface wave propagation allows more accurate modeling of the surface wave and improved assessments of tissue health Thus, it is contemplated that a layered surface wave model for the propagation of surface waves on skin may be utilized. Turning to FIG. 2, one such example employs three layers; however, it is noted that other numbers of layers may be utilized. In this case the layers may represent the dermis 202, subcutaneous fat 204, and muscle 206 having thicknesses $h_1$, $h_2$, and $h_3$, respectively. Because the muscle layer is much larger than the dermis and subcutaneous fat layers and because waves propagating downward from the dermis surface 202 decay rapidly, waves seldom reflect from the muscle layer to the skin surface. Accordingly, the muscle layer is assumed to be semi-infinite. That is, muscle layer thickness $h_3$ is considered infinite. There are two interfaces between the three layers, a dermis-fat interface 208 at depth $z_1$ and a fat-muscle interface 210 at depth $z_2$. The depth of each interface can be related to the thickness of layers above the interface by:

$$z_i = \sum_{n=1}^{i} h_n \quad \text{Eqn. 13}$$

$$i = 1, 2;$$

where z=0 is the surface of the skin. Each layer is assumed to be homogeneous and isotropic and the mass density and Lamb constants of each layer j=1,2,3 are respectively denoted as $\rho_j$, $\lambda_j$, and $\mu_j$. The properties of wave propagation in subsurface tissue layers, such the fat layer 204 and muscle layer 206, may be measured by an ultrasound probe 212. If using a point force to generate surface waves and assuming axially symmetric wave propagation, then only the normal displacement in the z-axis $\mu_{zj}$ and the displacement in the r-axis $\mu_{rj}$ need be considered. The differential equations for motion in the jth layer are:

$$(\lambda_j+2\mu_j)\left[\frac{\partial^2 u_{rj}}{\partial r^2}+\frac{1}{r}\frac{\partial u_{rj}}{\partial r}-\frac{u_{rj}}{\partial r^2}+\frac{\partial^2 u_{zj}}{\partial z \partial r}\right]+ \quad \text{Eqn. 14}$$

$$\mu_j\frac{\partial^2 u_{rj}}{\partial z^2}-\mu_j\frac{\partial^2 u_{zj}}{\partial z \partial r}=\rho_j\frac{\partial^2 u_{rj}}{\partial t^2}; \text{ and}$$

$$(\lambda_j+2\mu_j)\left[\frac{\partial^2 u_{rj}}{\partial r \partial z}+\frac{1}{r}\frac{\partial u_{rj}}{\partial z}+\frac{\partial^2 u_{zj}}{\partial z^2}\right]- \quad \text{Eqn. 15}$$

$$\frac{\mu_j}{r}\left(\frac{\partial u_{rj}}{\partial z}-\frac{\partial u_{zj}}{\partial z}\right)-\mu_j\left(\frac{\partial^2 u_{rj}}{\partial z \partial r}-\frac{\partial^2 u_{zj}}{\partial r^2}\right)=\rho_j\frac{\partial^2 u_{zj}}{\partial t^2}.$$

It is assumed that the layers are in contact at each interface and that $u_{rj}=u_{r(j+1)}$ and $u_{zj}=u_{z(j+1)}$ at $z=z_j$. The continuity of the normal and tangential stresses at the interface is also assumed as follows:

$$(p_{zz})_j = \lambda_j\nabla^2\varphi_1 + 2\mu_1\frac{\partial u_z}{\partial z}; \text{ and} \quad \text{Eqn. 16}$$

$$(p_{zr})_j = \mu_1\left(\frac{\partial \mu_r}{\partial z}+\frac{\partial \mu_z}{\partial r}\right). \quad \text{Eqn. 17}$$

The other set of boundary conditions are given by $p_{zz}=0$ and $p_{zr}=0$ at z=0 and $(p_{zz})_j=(p_{zz})_{j+1}$ and $(P_{zr})_j=(P_{zr})_{j+1}$ at $z=z_j$. The equations of motion can be solved by the compression wave potential $\phi_j$ and shear wave potential $\psi_j$, which are related to the displacements $u_{rj}$ and $u_{zj}$ by:

$$\mu_{rj} = \frac{\partial \varphi_j}{\partial r} + \frac{\partial^2 \varphi_j}{\partial r \partial z}; \text{ and} \quad \text{Eqn. 18}$$

$$\mu_{zj} = \frac{\partial \varphi_j}{\partial z} + \frac{\partial}{r \partial r}\left(-\frac{\partial \varphi_j}{\partial r}\right). \quad \text{Eqn. 19}$$

The two potentials $\psi_j$, and $\phi_j$ are solutions to the following wave equations:

$$\nabla^2\varphi_j = \frac{1}{\alpha_j^2}\frac{\partial^2\varphi_j}{\partial t^2}; \text{ and} \quad \text{Eqn. 20}$$

$$\nabla^2\psi_j = \frac{1}{\beta_j^2}\frac{\partial^2\psi_j}{\partial t^2}; \quad \text{Eqn. 21}$$

where $\alpha_j=\sqrt{(\lambda_j+2\mu_j)/\rho_j}$ and $\beta_j=\sqrt{\mu_j/\rho_j}$. For the layers of dermis and subcutaneous fat, both upward and downward traveling waves can be written as:

$$\varphi_j = \int_0^\infty Q_j J_0(kr)e^{-v_1(z-h)}dk + \int_0^\infty Q_j^* J_0(kr)e^{v_1(z-h)}dk; \quad \text{Eqn. 22}$$

and $$\psi_j = \int_0^\infty S_j J_0(kr)e^{-v_1(z-h)}dk + \int_0^\infty S_j^* J_0(kr)e^{v_1'(z-h)}dk; \quad \text{Eqn. 23}$$

where $Q_j$, $Q_j^*$, $S_j$, and $S_j^*$ are the functions satisfying the boundary conditions and $J_0(kr)$ is the Bessel function of the first kind. The two wave numbers in the layer are $v_j=\sqrt{k^2-k_{\alpha j}^2}$ and $v_j'=\sqrt{k^2-k_{\beta j}^2}$, where $k_{\alpha j}=\omega/\alpha_j$, $k_{\beta j}=\omega/\beta_j$, and $\omega$ is the frequency. As only the downward waves are retained for the muscle layer, these solutions can be written as:

$$\varphi_3 = \int_0^\infty Q_3 J_0(kr) e^{-v_3(z-h)} dk; \text{ and} \quad \text{Eqn. 24}$$

$$\psi_3 = \int_0^\infty S_3 J_0(kr) e^{-v_3(z-h)} dk. \quad \text{Eqn. 25}$$

Using harmonic force excitation, Eqns. 22 and 23 can be simplified for each layer as:

$$\phi_1 = A_1 e^{i(\omega t - kx) - v_1 z} + B_1 e^{i(\omega t - kx) + v_1 z} \quad \text{Eqn. 26}$$

$$\psi_1 = C_1 e^{i(\omega t - kx) - v_1' z} + D_1 e^{i(\omega t - kx) + v_1' z} \quad \text{Eqn. 27}$$

$$\phi_2 = A_2 e^{i(\omega t - kx) - v_2 z} + B_2 e^{i(\omega t - kx) + v_2 z} \quad \text{Eqn. 28}$$

$$\psi_2 = C_2 e^{i(\omega t - kx) - v_2' z} + d_2 e^{i(\omega t - kx) + v_2' z} \quad \text{Eqn. 29}$$

$$\phi_3 = A_3 e^{i(\omega t - kx) - v_3 z} \quad \text{Eqn. 30; and}$$

$$\Psi_3 = C_3 e^{i(\omega t - kx) - v_3' z} \quad \text{Eqn. 31}$$

There are ten unknown variables in the above equations. The boundary conditions at each interface of $z_1$ and $z_2$ must be satisfied, providing eight more equations, while at the skin surface, the normal and shear stresses are equal to zero, providing two more equations. Overall, there are ten equations for ten unknown variables and, for non-zero solutions, the determinant of the ten equations must be zero, that is:

$$\Delta = 0 \quad \text{Eqn. 32.}$$

This provides the characteristic wave equations from which the wave speed and dispersion of the surface wave and other waves in the layered skin model can be solved. Equation 32 can be reduced to a 4×4 matrix and further reduced to a single equation for satisfying boundary conditions using the transfer matrix method. The layered model can also be extended to more layers, including the epidermis, or simplified to a two-layered model for skin and subcutaneous fat. In this case, Equation 32 can be written as:

$$\begin{bmatrix} (2k^2 - k_{s1}^2) & (2k^2 - k_{s1}^2) & -2k^2\beta_1 & 2k^2\beta_1 & 0 & 0 \\ 2k\eta_1 & -2k\eta_1 & (2k^2 - k_{s1}^2) & (2k^2 - k_{s1}^2) & 0 & 0 \\ (2k^2 - k_{s1}^2)\mu_1 E_1^{-1} & (2k^2 - k_{s1}^2)\mu_1 E_1 & -2k\beta_1 B_1^{-1} & -2k\beta_1 B_1 & -(2k^2 - k_{s2}^2)\mu_2 E_2 & -2ik\beta_2\mu_2 E_2 \\ 2k\eta_1\mu_1 E_1^{-1} & -2k\eta_1\mu_1 E_1 & (2k^2 - k_{s1}^2)\mu_1 B_1^{-1} & -ikB_1 & 2ik\eta_2\mu_2 E_2 & -(2k^2 - k_{s2}^2)\mu_2 B_2 \\ ikE_1^{-1} & ikE_1 & -i\beta_1 B_1^{-1} & (2k^2 - k_{s1}^2)\mu_1 B_1 & -ikE_2 & \beta_2 B_2 \\ -i\eta_1 E_1^{-1} & -i\eta_1 E_1 & -ikB_1^{-1} & i\beta_1 B_1 & \eta_2 E_2 & -ikB_2 \end{bmatrix} = 0; \quad \text{Eqn. 33}$$

where $\eta_1 = \sqrt{k_{p1}^2 - k^2}$, $\beta_1 = \sqrt{k_{s1}^2 - k^2}$, $\eta_2 = \sqrt{k^2 - k_{p2}^2}$, $\beta_2 = \sqrt{k^2 - k_{s2}^2}$, $E_1 = \exp(i\eta_1 h_1)$, $B_1 = \exp(i\beta_1 h_1)$, $E_2 = \exp(-i\eta_2 h_1)$, and $B_2 = \exp(-\beta_2 h_1)$ in consistence with $k_{p1} = k_{\alpha 1}$, $k_{s1} = k_{\beta 1}$, $k_{p2} = k_{\alpha 2}$, and $k_{s2} = k_{\beta 2}$.

Figure 3:
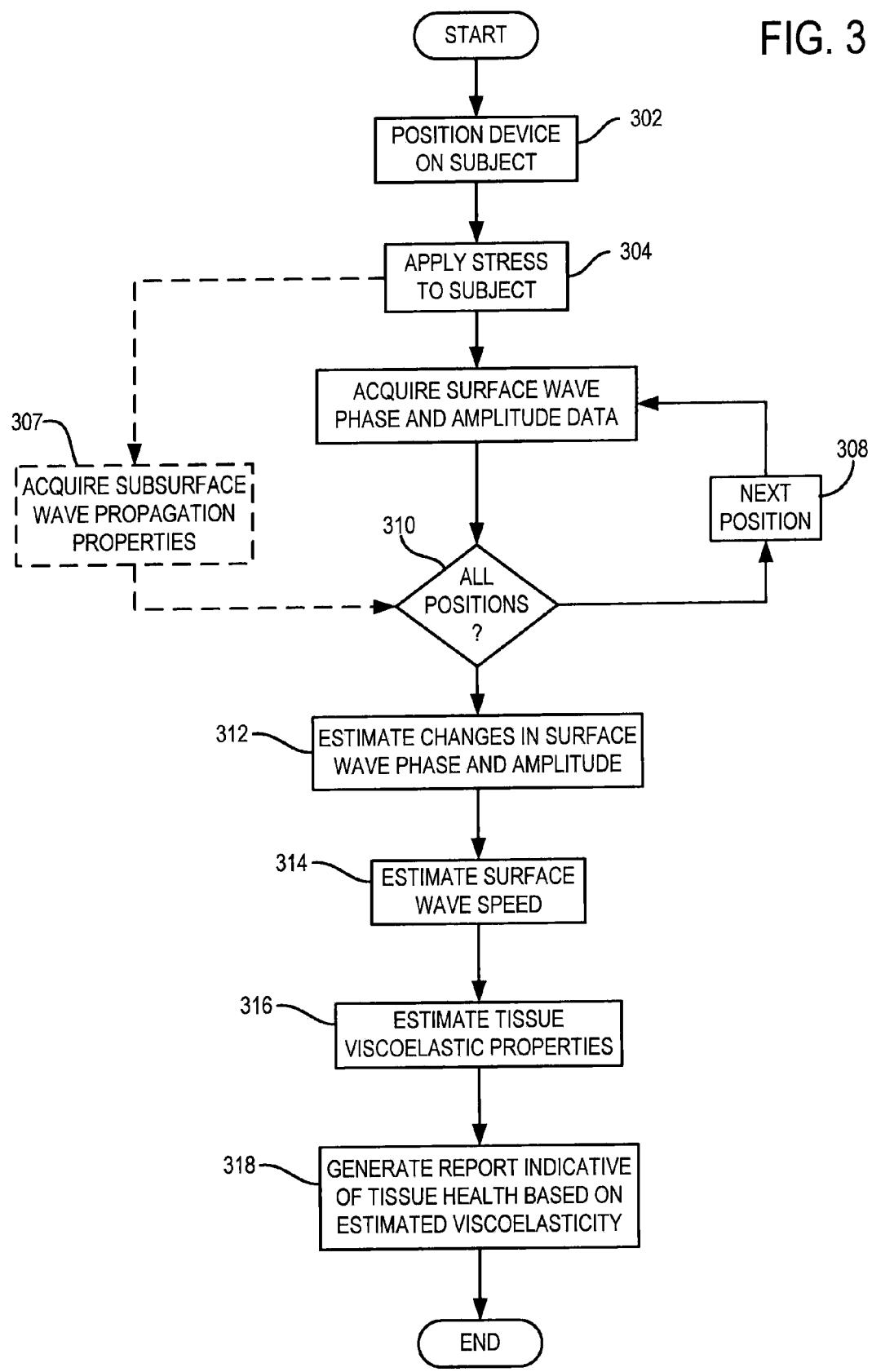
FIG. 3 is a flowchart setting for the steps for assessing tissue health using a single-layer surface wave model in accordance with the present invention.

Referring particularly to FIG. 3 and with reference to the devices of FIGS. 1 and 2, a method for assessing tissue health based on surface wave measurements starts at process block 302 with the positioning of the excitation and detection device 102 on the tissue being studied, for example, the surface of a subject's skin. At process block 304, a vibrating stimulus, for example, a 100 Hz 1 N vibration, is applied to the tissue by the driver 104 to produce surface waves that propagate through the through the tissue and become attenuated according to the tissue's mechanical properties. At process block 306, surface wave properties including phase and amplitude are measured by the detector 108. If employing a layered surface wave model, subsurface wave properties may also be acquired at this stage using, for example, an ultrasound transducer 212 as indicated at process block 307. This data may be employed by a layered surface wave model to provide improved characterization of surface wave propagation.

At process block 308, the detector is repositioned so that surface wave properties can be measured at different locations along the tissue. Measurement continues until, at decision block 310, surface wave properties have been acquired at a sufficient number of locations. It is contemplated that surface wave properties may be measured for a variety of frequencies. Therefore, the steps of process blocks 302 to 310 may be repeated for mechanical stimuli having different frequencies, allowing the calculation of properties such as wave speed dispersion.

At process block 312, changes in surface wave phase and amplitude with respect to distance are determined. At process block 314, $c_s$ is determined from the these changes in surface wave phase and amplitude using the following relationship:

$$c_s = 2\pi f \left| \frac{\Delta r}{\Delta \phi} \right|; \quad \text{Eqn. 33}$$

where $\Delta r$ is the radial distance between two measurement positions, $\Delta \phi$ is the surface wave phase change over that distance, and f is the frequency in Hz. It is contemplated that multiple measurements of $\Delta \phi$ and statistical may be acquired to provide more accurate estimates of $c_s$. For example, a regression curve obtained using a least-mean-squares (LMS) fitting technique on multiple $\Delta \phi$ measurements may be given by $\Delta \hat{\phi} = -\alpha \Delta r + \beta$, where $\Delta \hat{\phi}$ denotes the value of $\Delta \phi$ on the regression for a given distance $\Delta r$. Thus, $c_s$ can be estimated from the range of phase measurements using:

$$c_s = 2\pi f \left| \frac{\Delta r}{\Delta \hat{\phi}} \right| = 2\pi f / \alpha. \quad \text{Eqn. 34}$$

Figure 4:
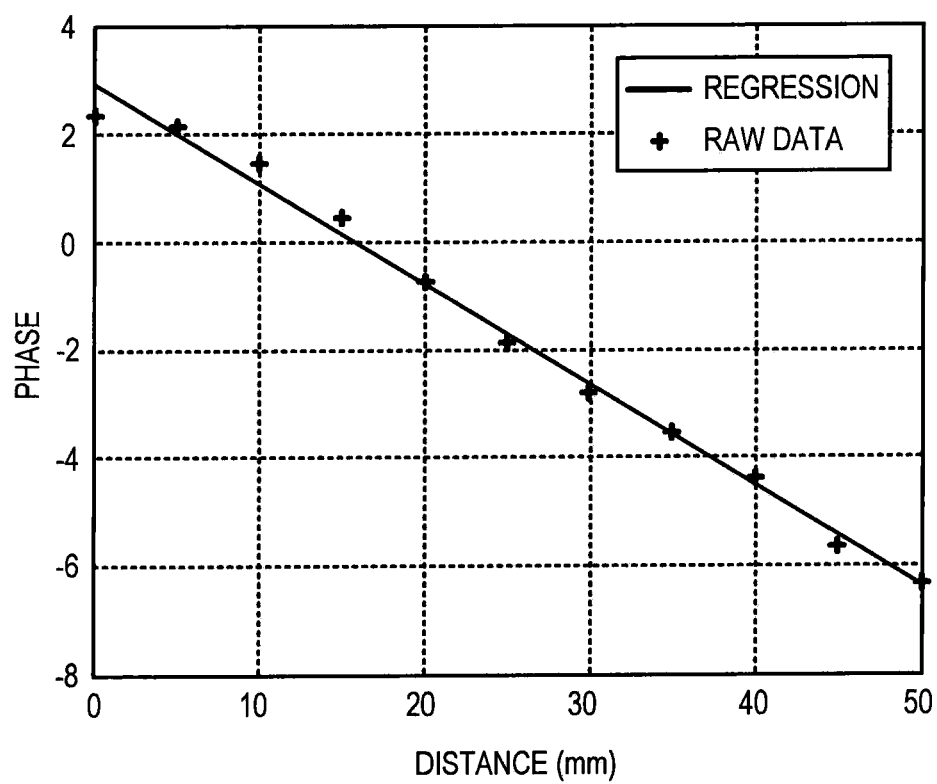
FIG. 4 is a regression curve showing a relationship between surface wave phase and distance in accordance with the present invention.

An exemplary regression analysis for a 400 Hz tone burst wave in a phantom is shown in FIG. 4. The regression equation, with the LMS of a 95 percent confidence interval, is $\Delta \hat{\phi} = -185.98 \Delta r + 2.91$, resulting in a surface wave speed estimate of 13.51 m/s. Likewise, regression analyses for 100 Hz, 200 Hz, and 300 Hz waves in the phantom provided wave speeds of 12.23 m/s, 12.74 m/s, and 13.06 m/s, respectively.

Referring back to FIG. 3, at process block 316, the viscoelastic properties of the tissue being studied are determined using the above-described surface wave propagation model. It is contemplated that this process may utilize a variety of models. For example, the viscoelastic modulus of the tissue may be calculated with Eqn. 13, using the estimated $c_s$ and Eqn. 6 to solve for Young's modulus E and the estimated changes in surface wave amplitude and Eqns. 12 and 14 to solve for β and γ. Likewise, Eqn. 12 and estimates of $c_s$ and wave dispersion and may be employed to determine tissue viscoelasticity according to the Voigt model.

At process block 318, a report indicative of the studied tissue's health is generated based on the determined viscoelasticity. For example, a report indicating the probability of scleroderma in the studied tissue may be produced by comparing the estimated viscoelastic properties to those of known healthy subjects and subjects having scleroderma. As mentioned previously, the surface wave propagation properties are not significantly changed by the driver or detector. Also, the estimated tissue viscoelasticity is a quantitative parameter. It is therefore contemplated that the present invention provides more accurate, reliable, and repeatable means for assessing tissue scleroderma with variability between examinations. By measuring wave speeds in different directions, the present invention may also be used to generate reports indicative of tissue health based on the anisotropic properties of skin. Because healthy skin typically has isotropic material properties, this may allow the early detection of disease or aging effects such as the formation of wrinkles.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for analyzing a tissue using a medical device, the method comprising the steps of:
   a) applying a stimulus to a selected location on the tissue to produce waves that propagate through the tissue with a driver;
   b) acquiring data indicative of a surface wave phase at a plurality of tissue locations with a detector; and using a processor for;
   c) estimating changes in surface wave phase with respect to distance;
   d) estimating a surface wave velocity from the estimated changes in surface wave phase with respect to distance;
   e) determining a viscoelastic property of the tissue from the estimated surface wave velocity using a surface wave model that relates the viscoelastic property to the estimated surface wave velocity; and
   f) generating a report indicative of at least one property of the tissue from the viscoelastic properties determined in step e).

2. The method as recited in claim 1 wherein the stimulus is applied using at least one of a mechanical shaker having a ball-tip applicator and a transducer.

3. The method as recited in claim 1 wherein the data indicative of surface wave phase is acquired using at least one of a laser vibrometer and an ultrasound transducer.

4. The method as recited in claim 3 wherein the laser vibrometer is configured to measure surface wave phase remotely from the tissue.

5. The method as recited in claim 3 wherein the ultrasound transducer is employed to measure wave propagation at selected depths within the tissue.

6. The method as recited in claim 1 wherein:
   step b) includes acquiring data indicative of surface wave amplitude at the plurality of tissue locations;
   step c) includes estimating changes in surface wave amplitude with respect to distance; and
   the viscoelastic property of the tissue is determined from the estimated surface wave velocity and the estimated changes in surface wave amplitude.

7. The method as recited in claim 6 wherein the viscoelastic property of the tissue is determined from the estimated surface wave velocity and the estimated changes in surface wave amplitude using the relationship:

$$c_s = \frac{1}{1.05}\sqrt{\frac{E}{3\rho}}$$

in which $c_s$ is the estimated surface wave speed, E is an elasticity parameter of the tissue, and ρ is the density of the tissue.

8. The method as recited in claim 1 wherein the viscoelastic property of the tissue is determined from the estimated surface wave velocity using the relationship:

$$c_s = \frac{1}{1.05}\sqrt{\frac{2(\mu_1^2 + \omega^2\mu_2^2)}{\rho(\mu_1 + \sqrt{(\mu_1^2 + \omega^2\mu_2^2)})}}$$

in which $c_s$ is the estimated surface wave speed, ω is a surface wave frequency, $\mu_1$ is a shear elasticity parameter of the tissue, $\mu_2$ is a shear viscosity parameter of the tissue; and ρ is a density of the tissue.

9. The method as recited in claim 8 wherein the viscoelastic property of the tissue is determined from the estimated surface wave velocity and a wave dispersion parameter.

10. The method as recited in claim 9 wherein the wave dispersion parameter is estimated by performing steps a) to c) for stimuli having different frequencies and analyzing changes in surface wave phase with respect to the different frequencies.

11. The method as recited in claim 1 wherein the surface wave model used in step e) is at least one of a single layer surface wave model and layered surface wave model.

12. The method as recited in claim 1 wherein the at least one property of the tissue is indicative of scleroderma for the tissue.

13. The method as recited in claim 1 wherein the at least one property of the tissue is indicative of an anisotropic property of the tissue.

14. A medical device for assessing the health of a tissue, the device comprising;
   a driver configured to apply a stimulus to the tissue and produce waves that propagate through the tissue;
   a detector configured to acquire data indicative of surface wave phase at a plurality of tissue locations;
   a processor in communication with the detector configured to estimate changes in surface wave phase with respect to distance, estimate a surface wave speed, determine a viscoelastic property of the tissue from the estimated surface wave speed, and generate a report indicative of the health of the tissue; and
   wherein the processor employs a surface wave model to determine the viscoelastic property of the tissue from the estimated surface wave speed and generate the report indicative of the health of the tissue.

15. The device as recited in claim 14 wherein the processor employs a surface wave model that is at least one of a single-layer surface wave model and a layered surface wave model.

16. The device as recited in claim 14 wherein the driver is at least one of a mechanical shaker having a ball-tip applicator and a transducer and the detector is at least one of a laser vibrometer and a ultrasound transducer.

17. The device as recited in claim 14 wherein the detector is further configured to acquire data indicative of surface wave amplitude at the plurality of tissue locations and the processor is further configured to estimate changes in surface wave amplitude with respect to distance.

18. The device as recited in claim 14 wherein the driver is further configured to apply the stimulus to the tissue at a plurality of different frequencies, the detector is further configured to acquire the data indicative of surface wave phase at each of the different frequencies, and the processor is further configured to estimate surface wave speed dispersion from changes in surface wave phase with respect to the different frequencies.

19. The method as recited in claim 1 in which the surface wave model used in step e) is based on at least one wave equation.

20. The device as recited in claim 14 wherein the processor employs a surface wave model that is based on at least one wave equation.

\* \* \* \* \*

UNITED STATES PATENT AND TRADEMARK OFFICE
CERTIFICATE OF CORRECTION

PATENT NO. : 9,044,192 B2
APPLICATION NO. : 12/418111
DATED : June 2, 2015
INVENTOR(S) : James F. Greenleaf et al.

It is certified that error appears in the above-identified patent and that said Letters Patent is hereby corrected as shown below:

In the Specification,

Column 6, line 41 - "$\in$" should be --$\xi$--

Column 9, equation 29 - "d" should be --D--

Signed and Sealed this
Twenty-ninth Day of September, 2015

Michelle K. Lee
*Director of the United States Patent and Trademark Office*